United States Patent
Igarashi et al.

(10) Patent No.: US 6,448,320 B1
(45) Date of Patent: Sep. 10, 2002

(54) SUPERABSORBENT RESIN COMPOSITION AND METHOD FOR PRODUCING THE SAME

(75) Inventors: Tadashi Igarashi; Yoko Hanada; Hisakazu Furugaki, all of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/015,906

(22) Filed: Jan. 30, 1998

(30) Foreign Application Priority Data

Jan. 31, 1997 (JP) .............................................. 9-019232
Sep. 4, 1997 (JP) .............................................. 9-239319

(51) Int. Cl.[7] .................................................. C08K 5/09
(52) U.S. Cl. ...................................... 524/394; 524/320
(58) Field of Search .................................. 524/394, 320

(56) References Cited

U.S. PATENT DOCUMENTS

| | | | | |
|---|---|---|---|---|
| RE28,957 E | * | 9/1976 | Drelich et al. ............... | 427/331 |
| 5,854,304 A | * | 12/1998 | Garcia et al. ................ | 523/124 |
| 5,985,944 A | * | 11/1999 | Ishizaki et al. ............... | 521/64 |

FOREIGN PATENT DOCUMENTS

| | | | |
|---|---|---|---|
| EP | 0621041 A1 | | 10/1994 |
| EP | 0702031 A2 | | 3/1996 |
| EP | 889063 A1 | * | 1/1999 |
| FR | 2310156 | | 12/1976 |
| FR | 2682389 | | 4/1993 |
| JP | 56-89838 | | 7/1981 |
| JP | 59-230046 | | 12/1984 |
| JP | 60-18690 | | 5/1985 |
| JP | 61-211305 | | 9/1986 |
| JP | 61-48521 | | 10/1986 |
| JP | 61-264006 | | 11/1986 |
| JP | 62-36411 | | 2/1987 |
| JP | 1275661 | | 11/1989 |
| JP | 519563 | | 3/1993 |
| JP | 6306118 | | 11/1994 |
| JP | 7145326 | | 6/1995 |
| WO | WO 9605234 | | 2/1996 |

OTHER PUBLICATIONS

Japan Patent abstract (JP 02000026738A) Hosokawa et al., High water–absorbing resin composition Jan. 25, 2000.*
Japan Patent abstract (JP 2883330B) Hosokawa et al., Water absorber for disposable diaper, sanitary towel etc. Apr. 19, 1999.*
Japanese Patent document 2883330 B1 (abstract); Kao KK [KAOS]; Water absorber for disposable diaper, sanitary towel, etc., Apr. 19, 1999.*
J. Am. Chem. Soc., "Metal Ion and Metal Chelate Catalyzed Oxidation of Ascorbic Acid by Molecular Oxygen. I. Cupric and Ferric Ion Catalyzed Oxidation", Vol. 89:16, pp. 4176–4185, Aug. 2, 1967.
Free Radical Research Communication, "Ascorbate Autoxidation in the Presence of Iron and Copper Chelates", vol. 4, pp. 63–71 (1967).
Carbohydrate Research, "Depolymerization of Some Polysaccharides and Synthetic Polymers by L–Ascorbic Acid*", vol. 4, pp. 63–71 (1967).

* cited by examiner

*Primary Examiner*—Hoa Van Le
*Assistant Examiner*—Yvette M. Clarke
(74) *Attorney, Agent, or Firm*—Birch, Stewart, Kolasch & Birch, LLP

(57) ABSTRACT

The superabsorbent resin composition of the present invention comprises (A) a superabsorbent resin and (B) a metal compound obtained by mixing a hydroxy acid or a salt thereof and a polyvalent metal salt or polyvalent metal alkoxide having at least one metal selected from the group consisting of titanium and zirconium. The method for producing a superabsorbent resin composition comprises mixing the components (A) and (B).

8 Claims, No Drawings

SUPERABSORBENT RESIN COMPOSITION AND METHOD FOR PRODUCING THE SAME

BACKGROUND OF THE INVENTION

1. Field of the Invention

The present invention relates to a superabsorbent resin composition which has high water absorption and undergoes neither degradation nor deterioration even in a water-containing state after it absorbs aqueous liquids or body fluids, such as urine, blood and perspiration; and to a method for producing the same.

2. Description of Related Art

Superabsorbent resins have been widely used as a water-absorbing material in absorbent articles in the sanitary field, such as disposable diapers for babies, adults or those suffering from incontinence, and sanitary napkins; as water-retaining materials in the agricultural and horticultural fields; and as sludge coagulants, moisture condensation preventive agents, and water stopping agents in the field of civil engineering.

It is known that water-soluble polymers (crosslinked polymers) constituting such superabsorbent resins undergo molecular weight reduction (degradation) and deterioration with time in the presence of radical generating species, such as hydrogen peroxide or L-ascorbic acid or a salt thereof. Because L-ascorbic acid or a salt thereof is present in body fluids, such as urine, blood, and perspiration, superabsorbent resin degradation and deterioration in disposable diapers or sanitary napkins has been a serious problem.

The degradation reaction of a water-soluble polymer due to such radical generating species is conspicuous after the polymer has absorbed an aqueous liquid or a body fluid, such as urine, blood or perspiration (hereinafter referred to as a water-containing condition), especially in the co-presence of transition metal ions capable of having more than one oxidation number, such as iron ions or copper ions, in the air.

This is because traces of transition metal ions, such as iron or copper, serve as a catalyst to markedly accelerate decomposition and radical generation of hydrogen peroxide or L-ascorbic acid or a salt thereof, as described, e.g., in *J. Am. Chem. Soc.*, Vol. 89, p. 4176 (1967) and *Carbohydrate Research*, Vol. 4, p. 63 (1967).

While such transition metal ions are sometimes added intentionally or as a third component to a system containing a superabsorbent resin and a radical generating species, e.g., hydrogen peroxide or L-ascorbic acid or a salt thereof, metallic ions are present in water or raw materials as impurities in a very trace amounts, and it is known that such extremely small amounts of transition metal ions can have sufficient catalyzing activity for severing the water-soluble high-molecular weight chains of the superabsorbent resin over time (see, for example, *Free Radical Research Communications*, Vol. 1, p. 349 (1986)).

Known approaches for inhibiting the above-described degradation and deterioration of superabsorbent resins include (1) a method comprising sealing the superabsorbent resin under reduced pressure, or in a nitrogen atmosphere so as to avoid contact with air (especially oxygen), (2) a method comprising using highly purified water or raw materials so as to prevent metallic ions from entering the superabsorbent resin, (3) a method comprising adding an antioxidant or a reducing agent to the superabsorbent resin, (4) a method of adding proteins or enzymes to the superabsorbent resin, and (5) a method of adding to the superabsorbent resin, metal chelating agents, such as citric acid, (poly)phosphoric acid or a salt thereof, and ethylenediaminetetraacetic acid (EDTA) or a salt thereof.

However, the methods (1) and (2) are in many cases practically impossible to apply depending on the use of the superabsorbent resin. Methods (3), (4), and (5) that rely on conventional additives achieve some effect in suppressing degradation and deterioration of superabsorbent resins but are not always sufficient in effect. In many cases, an additive must be added in a large quantity or an additive exerting a very strong action must be used before the desired effect can be manifested. Under such circumstances, the essential physical properties or functions of the superabsorbent resin tend to be seriously ruined, and some of the additives can bring about unfavorable results in terms of the hygiene of the working environment, i.e., some emit an offensive odor, and some have poor stability.

Mixing or dispersing a metal chelating agent in a superabsorbent resin is disclosed in Japanese Patent Laid-Open Nos. 89838/81, 230046/84, and 275661/89. For example, it has been revealed that the water-absorbing performance is not reduced even in the presence of water containing salts or ions by using EDTA, sodium tripolyphosphate, etc.

According to the inventors' study, however, it has turned out that the use of EDTA or sodium tripolyphosphate is not so effective in stabilizing a superabsorbent resin in the presence of an aqueous solution or water containing a radical generating species, e.g., hydrogen peroxide or L-ascorbic acid or a salt thereof.

In addition to the above-mentioned performance properties of superabsorbent resins, i.e., stability over time in a water-containing state (gel stability with time), the water absorption capacity (the amount of water absorbed), the rate of water absorption, the gel strength after swelling, liquid permeability, and the like are important requirements for superabsorbent resins. However, many of these properties conflict with each other, and it is very difficult to meet all of these requirements, which has been one of the problems in developing superabsorbent resins. For example, an attempt to increase water absorption is generally accompanied by reductions in gel strength after swelling and liquid permeability.

Various methods have recently been proposed in order to solve these problems. For example, Japanese Patent Publication Nos. 18690/85 and 48521/86 propose forming a highly crosslinked layer as a surface layer of a superabsorbent resin. Japanese Patent Publication No. 19563/93, and Japanese Patent Laid-Open Nos. 211305/86, 264006/86, and 36411/87 propose graft-treating a carboxyl- and/or carboxylate-containing superabsorbent resin with a silane coupling agent. Japanese Patent Laid-Open No. 306118/94 proposes treating a superabsorbent resin with a titanium alkoxide. Additionally, a method comprising spraying an aqueous solution of a compound capable of reacting easily with a functional group of a superabsorbent resin (e.g., a carboxylate group), such as an aqueous solution of a polyvalent metal salt, a polyglycidyl ether, or a polyisocyanate, onto a superabsorbent resin, followed by heating to form a highly crosslinked layer on the surface of the superabsorbent resin is known. Nevertheless, these methods are still insufficient for satisfying both superabsorbent performance (e.g., a water absorption capacity) and gel stability with time after swelling.

Japanese Patent Laid-Open No. 145326/95 discloses the addition of a sulfate of a polyvalent metal selected from titanium, zirconium and vanadium to a superabsorbent polymer as one method for simultaneously improving gel strength, stability, and stickiness after water absorption.

According to the inventors' study, however, the gel stability over time achieved by this method is insufficient particularly for polymers having high water absorption. Besides, addition of a polyvalent metal sulfate tends to reduce the initial rate of water absorption of the superabsorbent polymer or tends to make the polymer particles before water absorption ready to agglomerate due to the hygroscopicity of the polyvalent metal sulfate.

SUMMARY OF THE INVENTION

An object of the present invention is to provide a superabsorbent resin composition which exhibits high water absorption and is yet stable against degradation and/or deterioration even in the presence of an aqueous solution or water containing a radical generating species, such as L-ascorbic acid or a salt thereof, or a transition metal ion, such as an iron ion or a copper ion.

In particular, the object of the present invention is to provide a superabsorbent resin composition which has a high water absorption and undergoes neither degradation nor deterioration even in a water-containing state after it absorbs aqueous liquids or body fluids, such as urine, blood and perspiration; especially a superabsorbent resin composition which can be added to an absorbent member of sanitary articles such as paper diapers thereby enhancing the urine resistance of the sanitary articles.

As a result of extensive study, the inventors have found that the above object is accomplished by a superabsorbent resin composition containing a superabsorbent resin and a specific metal compound.

The present invention has been achieved based on the above finding. The present invention provides a superabsorbent resin composition comprising (A) a superabsorbent resin and (B) a metal compound obtained by mixing a hydroxy acid or a salt thereof and a polyvalent metal salt or polyvalent metal alkoxide having at least one metal selected from the group consisting of titanium and zirconium.

The present invention also provides a method for producing a superabsorbent resin composition comprising mixing (A) a superabsorbent resin and (B) a metal compound obtained by mixing a hydroxy acid or a salt thereof and a polyvalent metal salt or polyvalent metal alkoxide having at least one metal selected from the group consisting of titanium and zirconium.

The superabsorbent resin composition according to the present invention is effective where a superabsorbent resin is used in combination with cosmetics or food additives containing a radical generating species, such as L-ascorbic acid or a salt thereof, while depending on the kind of the superabsorbent resin. It is also effectively used as a water-absorbing material in sanitary articles. The superabsorbent resin composition of the present invention is particularly suited for use as a water-absorbing material in sanitary articles, specifically a water-absorbing material added to an absorbent member of an absorbent article comprising a water-permeable topsheet, a water-impermeable backsheet and an absorbent member interposed between the topsheet and backsheet. In addition, component (B) in the superabsorbent resin composition of the present invention exhibits an excellent effect as a urine-resistance improver.

The superabsorbent resin composition of the present invention is excellent in that it has high water absorption and yet the superabsorbent resin used therein does not undergo degradation or deterioration even in the presence of an aqueous solution or water containing radical generating species, such as L-ascorbic acid or a salt thereof, or transition metal ions, such as iron or copper ions.

The method according to the present invention provides a superabsorbent resin composition exhibiting the above-mentioned excellent performance.

DETAILED DESCRIPTION OF THE PREFERRED EMBODIMENTS

The superabsorbent resin composition of the present invention will now be described below in detail.

The superabsorbent resin which can be used in the present invention as component (A) is not particularly limited and includes, for example, polymers containing a carboxyl group or a salt thereof, such as a crosslinked polyacrylic acid salt, a poly(vinyl alcohol/acrylic acid salt) copolymer, a crosslinked poly(vinyl alcohol/acrylic acid salt) copolymer, a starch-acrylic acid salt graft copolymer, a crosslinked starch-acrylic acid salt graft copolymer, a polyvinyl alcohol-polymaleic anhydride salt graft copolymer, and a crosslinked polyvinyl alcohol-polymaleic anhydride salt graft copolymer, and partially crosslinked polysaccharides, such as a crosslinked carboxymethyl cellulose salt. A crosslinked polyacrylic acid salt, a starch-acrylic acid salt graft copolymer and a crosslinked starch-acrylic acid salt graft copolymer are preferably used for their high water absorbability. A crosslinked polyacrylic acid salt is the most preferred.

These superabsorbent polymers can be used either individually or as a combination of two or more thereof.

A "salt" of the superabsorbent resins illustrated above includes an alkali metal salt (e.g., sodium salt, potassium salt or lithium salt), an alkaline earth metal salt (e.g., calcium salt, magnesium salt or barium salt), and an ammonium salt (e.g., a quaternary ammonium salt or a quaternary alkylammonium salt).

The superabsorbent resin preferably has a degree of neutralization of 0.01 to 100%, still preferably 1 to 99%, particularly preferably 40 to 95%, based on the number of moles of the acid radical in the superabsorbent resin.

The terminology "degree of neutralization" as used herein denotes a molar ratio of acid radicals in a salt form to the total acid radicals of a superabsorbent resin, i.e., (the number of moles of acid radicals in salt form)/(the total number of moles of free acid radicals capable of forming a salt and acid radicals in salt form)×100 (%).

The metal compound which can be used in the present invention as component (B) is a metal compound obtained by mixing a hydroxy acid or a salt thereof and a polyvalent metal salt or polyvalent metal alkoxide having at least one metal selected from the group consisting of titanium and zirconium (hereinafter referred to as metal A).

The hydroxy acid is a compound having a hydroxyl group and a carboxyl group per molecule and is not particularly limited in kind. Examples of suitable hydroxy acids are α-hydroxy acids. Where hydrolysis is conducted in the preparation of the metal compound as component (B) as hereinafter described, it is desirable for the hydrolyzate be water-soluble. Accordingly, water-soluble hydroxy acids are preferred. Water-soluble α-hydroxy acids are still preferred. Examples of such α-hydroxy acids are gluconic acid, citric acid, isocitric acid, alloisocitric acid, lactic acid, hydroxyacetic acid, malic acid, and tartaric acid, with gluconic acid and citric acid being particularly preferred.

Examples of salts of the above-enumerated hydroxy acids include alkali metal salts (e.g., sodium salt, potassium salt, and lithium salts), alkaline earth metal salts (e.g., calcium salt, magnesium salt, and barium salt), and ammonium salts (e.g., quaternary ammonium salts and quaternary alkylammonium salts).

These hydroxy acids and salts thereof can be used either individually or as a mixture of two or more thereof.

The metal A is one or both of titanium and zirconium. In other words, titanium and zirconium can be used either alone or in combination. Titanium is preferred as metal A from the standpoint of the degree of improvement attained and cost.

The polyvalent metal salt made of metal A is not particularly limited and includes a sulfate, an oxysulfate, a chloride, an oxychloride, a nitrate, an oxynitrate, and a carboxylate of metal A. A sulfate, an oxysulfate, a chloride, and an oxychloride are preferred, with a sulfate and a chloride being still preferred.

The alkoxide of metal A includes a tetraisopropoxide and a tetrabutoxide of metal A.

When a hydroxy acid or a salt thereof and a polyvalent metal salt or polyvalent metal alkoxide are mixed, they are preferably mixed in the form of an aqueous solution or an alcoholic solution. In particular, where a polyvalent metal salt is used, they are preferably mixed in the form of an aqueous solution, and where a metal alkoxide is used, they are preferably mixed in the form of an alcoholic solution. When mixed as an aqueous solution or an alcoholic solution, the system provides a more effective metal compound (component (B)).

The hydroxy acid or a salt thereof is preferably used in an amount of not less than twice the molar quantity of metal A in the polyvalent metal salt or alkoxide. If the molar ratio is less than 2, the system, i.e., a mixed solution, tends to become heterogeneous, which is unfavorable for the effects and handling properties discussed above.

It is preferable that the hydroxy acid or a salt thereof and the polyvalent metal salt or alkoxide be not only mixed but that the latter be hydrolyzed in the presence of the former. In this case, a more effective metal compound as component (B) is obtained.

Where the polyvalent metal salt or alkoxide is hydrolyzed, the method of hydrolysis is not particularly restricted. Various techniques of hydrolysis can be employed. For example, a base, such as sodium hydroxide, potassium hydroxide, ammonia, amine, etc., is added, and, if necessary, the system is heated.

An illustrative example of the hydrolysis conditions is as follows. The base is preferably added in an amount 2 to 4 times the molar quantity of the metal A. The temperature of heating, if conducted, is preferably 60 to 100° C. The hydrolyzing time is preferably 20 to 60 minutes. Water, preferably ion-exchanged water, is used in an amount of 100 to 1000 parts by weight per 100 parts by weight of the polyvalent metal salt or polyvalent metal alkoxide.

Where hydrolysis is carried out, it is preferable for the hydrolyzate, inclusive of the metal compound as component (B), to be water-soluble. If the hydrolyzate has low water solubility and has a high insoluble content, the effects and handling properties are poor.

While the state of the resulting metal compound as component (B) in the preparation of a superabsorbent resin composition hereinafter described is not particularly limited, the metal compound is preferably in the form of an aqueous or alcoholic solution (or, where hydrolysis is conducted, in the form of a hydrolyzate solution as obtained by hydrolysis). The metal compound solution preferably has a metal A concentration of 0.05 to 5% by weight, particularly 0.2 to 2% by weight.

Metal A in component (B) is preferably used in an amount of 0.001 to 1 part by weight, particularly 0.005 to 0.5 part by weight, especially 0.01 to 0.1 part by weight, per 100 parts by weight of a superabsorbent resin in water-free dry state as component (A).

If the metal A content is less than 0.001 part by weight, the resulting resin composition has insufficient gel stability. Even if the content exceeds 1 part by weight, little further improvement is expected. Accordingly, the above-described range is preferred.

The superabsorbent resin composition of the present invention can contain also water, in addition to the superabsorbent resin as component (A) and the metal compound as component (B). In this embodiment, the superabsorbent resin is a water-containing polymer or the composition is in a water-containing gel state. The superabsorbent resin composition can contain water within its absorptive capacity.

If desired, the superabsorbent resin composition can contain various additives, such as a water-soluble organic solvent, a surface active agent, a salt, inorganic fine particles, a stabilizer, a chelating agent, an antioxidant, a reducing agent and/or an antiseptic. Water and these additives can be added in an total amount of not more than 50% by weight based on the total weight superabsorbent resin composition.

The superabsorbent resin composition is prepared, for example, according to the following methods (1) to (3).

(1) A method comprising previously adding the metal compound to the preparation system for making the superabsorbent resin. For example, in using a water-soluble vinyl monomer for providing a superabsorbent resin, the metal compound is added to the water-soluble vinyl monomer, and the monomer is then polymerized.

(2) A method comprising spraying an aqueous solution of the metal compound onto the superabsorbent resin in a dry state or a water-containing state and, if desired, drying the resin.

(3) A method comprising dry mixing the superabsorbent resin and the metal compound.

While the water absorption of the superabsorbent resin composition according to the present invention is not particularly limited, it is preferable for the composition to have a water holding power of 35 g/g or more, particularly 38 g/g or more, as measured in accordance with a holding power measuring method by centrifugal dehydration hereinafter described.

In general, as the water absorption of the superabsorbent resin composition increases, the amount of resin required per article, e.g., diaper, decreases, which contributes to reductions in the thickness of the diaper and manufacturing cost. However, as the water absorption increases, the performance properties, such as gel stability over time, gel strength, and liquid permeability, are generally reduced. Therefore, resins exhibiting super absorptivity are difficult to apply to disposable diapers. To the contrary, the superabsorbent resin composition according to the present invention has a relatively high water absorption having a holding power of 35 g/g or more and yet hardly undergoes such reductions in performance.

As stated above, the superabsorbent resin composition of the present invention is particularly useful as a water-absorbing material in sanitary articles, such as absorbent articles, e.g., disposable diapers and sanitary napkins. Such absorbent articles comprise a water-permeable topsheet, a water-impermeable backsheet and an absorbent member interposed between said topsheet and said backsheet. The materials of the absorbent member include cellulose fibers, synthetic fibers or mixture thereof which are commonly used as the material of the absorbent member of the absorbent article, e.g., fluff pulp, i.e., ground wood pulp. The superabsorbent resin composition is used in combination with the materials of the absorbent member, preferably with the fluff pulp as a mixture with the materials of the absorbent member, such as the fluff pulp or in the form of an independent layer on specific areas of a layer of the materials of the absorbent member, such as the fluff pulp. In another embodiment, the absorbent member can be prepared by heat treating a mixture of a thermoplastic resin, fluff pulp, and the superabsorbent resin composition of the present invention.

The superabsrobent resin composition of the present invention can be adequately added, according to the object, in a total amount of 30 to 80 parts by weight based on 100 parts by weight of the absorbent member.

Because body fluids such as urine contain L-ascorbic acid or a salt thereof superabsorbent resin in a conventional superabsorbent resin composition deteriorates by such substances present in body fluids absorbed by the absorbent articles. To the contrary, where the superabsorbent resin composition of the present invention is used as a water-absorbing material of absorbent articles, deterioration of the superabsorbent resin can be suppressed.

Moreover, the superabsorbent resin composition of the present invention has high gel strength and high liquid permeability after swelling, and is therefore suitable for use in absorbent articles, such as disposable diapers and sanitary napkins.

The method for producing the superabsorbent resin composition of the present invention will now be described below in detail.

The method of preparation comprises mixing components (A) and (B). Mixing can be carried out by, for example, by adhering component (B) on the surface of component (A) or mixing them both in a dry state. In one embodiment as component (A), a superabsorbent resin is obtained by polymerizing a water soluble vinyl monomer in the presence of a metal compound as component (B). In such a superabsorbent resin, components (A) and (B) are present in a uniformly mixed state.

In polymerizing the water-soluble vinyl monomer, the manner how to include component (B) in the reactant system is not particularly limited, and the metal compound can be added in the course of the polymerization of the water-soluble vinyl monomer. It is possible to add the metal compound as a solution, either as dissolved in an appropriate solvent, if desired, or as obtained in the form of a mixed solution. More specifically, the following methods (i) to (iii) are possible.

(i) A method for producing a superabsorbent resin composition comprising the steps of:
  (a) mixing a hydroxy acid or a salt thereof and a polyvalent metal salt of a metal A (i.e., at least one metal selected from the group consisting of titanium and zirconium) or an alkoxide of the metal A in a liquid medium to prepare a mixture,
  (b) mixing a water-soluble vinyl monomer and the mixture obtained in the step (a), and
  (c) polymerizing the water-soluble vinyl monomer to obtain a polymer, and drying the polymer to obtain a superabsorbent resin composition.

(ii) A method for producing a superabsorbent resin composition comprising the steps of:
  (a) mixing a hydroxy acid or a salt thereof and a polyvalent metal salt of a metal A (i.e., at least one metal selected from the group consisting of titanium and zirconium) or an alkoxide of the metal A in a liquid medium to prepare a mixture, and
  (b') mixing a polymerization reaction system of a water-soluble vinyl monomer with the mixture obtained in the step (a) while continuing polymerization of the water-soluble vinyl monomer, and drying the resulting polymer to obtain a superabsorbent resin composition.

(iii) A method for producing a superabsorbent resin composition comprising the steps of:
  (a) mixing a hydroxy acid or a salt thereof and a polyvalent metal salt of a metal A (i.e., at least one metal selected from the group consisting of titanium and zirconium) or an alkoxide of the metal A in a liquid medium to prepare a mixture, and
  (b") mixing a polymer of a water-soluble vinyl monomer and the mixture obtained in the step (a) and, optionally drying the mixture thus obtained to thereby give a superabsorbent resin composition.

While polymerization of the water-soluble vinyl monomer can be carried out by any process, a process comprising subjecting an aqueous solution of the water-soluble vinyl monomer (preferably a solution having a monomer concentration of 1 to 70% by weight) to a polymerization system is preferred. For example, solution polymerization, reversed phase suspension polymerization. pearl polymerization, or a like polymerization technique can be adopted. In view of polymerization workability and absorption performance of the resulting superabsorbent resin, solution polymerization and reversed phase suspension polymerization are preferably employed. In particular, reversed phase suspension polymerization is preferred from the viewpoint of absorption performance.

The water-soluble vinyl monomer to be used is not particularly limited and includes those which are capable of polymerizing to provide the above-enumerated superabsorbent resin (component (A)) used in the resin composition of the present invention. From the viewpoint of cost and performance of the resulting superabsorbent resin, those containing at least 50% by weight of at least one monomer selected from the group consisting of acrylic acid, an alkali metal acrylate, and ammonium acrylate are useful.

It is desirable that the water-soluble vinyl monomer be homopolymerized or two or more of the water-soluble vinyl monomers be copolymerized. It is also possible to copolymerize the water-soluble vinyl monomer and not more than 50% by weight, based on the total monomers, of a water-insoluble vinyl monomer copolymerizable with the water-insoluble vinyl monomer.

In polymerizing the water-soluble vinyl monomer(s), a known polymerization initiator is employed. If desired, a known crosslinking agent can be added before, during or after polymerization or during drying. A modifier can be used as well. The amounts of these additives are not particularly limited as long as the effects of the present invention are not impaired.

The polymerization of the water-soluble vinyl monomer (s) is preferably carried out at a temperature of 20 to 120° C. for a period of 20 to 180 minutes.

It is preferable to carry out the polymerization of the water-soluble vinyl monomer(s) in the presence of 0.001 to 1 part by weight, particularly 0.005 to 0.5 part by weight, especially 0.01 to 0.1 part by weight, in terms of metal (A), of the metal compound as component (B) per 100 parts by weight of the water-soluble vinyl monomer. When the metal A content in the polymerization system falls within the above range, a superabsorbent resin composition having enhanced effects can be obtained.

It is preferable to use, as component (B), a metal compound obtained by using an α-hydroxy acid as a hydroxy acid and titanium as a metal A. In this case, a superabsorbent resin composition exerting further improved effects can be obtained.

The present invention will now be illustrated in greater detail by way of the Examples and in view of the Comparative Examples, but the present invention should not be construed as being limited thereto. Unless otherwise indicated, all the percents and parts are given by weight.

The test methods used in the Examples and Comparative Examples are described below.

1) Measurement of Holding Power by Centrifugal Dehydration Method:

A superabsorbent resin composition weighing 1 g was swollen with 150 ml of physiological saline (0.9% NaCl solution, produced by Otsuka Pharmaceutical Co., Ltd.) for 30 minutes and put in a bag made of nonwoven fabric. The bag and the contents were dehydrated in a centrifugal separator at 143G for 10 minutes and weighed (overall weight). The holding power after centrifugal dehydration was calculated according to equation (1).

Holding power after centrifugal dehydration (g/g)=[(overall weight)−(weight of nonwoven fabric bag)−(weight of superabsorbent resin composition)−(residue of liquid in nonwoven fabric bag)]/(weight of superabsorbent resin composition)     (1)

2) Evaluation of Gel Stability with Time after Swelling:

A superabsorbent resin composition weighing 1 g was swollen with 45 g of physiological saline containing 0.05% of L-ascorbic acid. The swollen resin composition was sealed in a screw tube and allowed to stand at 40° C. for 3 hours. The state of the swollen gel after the standing was observed to evaluate the gel stability with time. The evaluation on gel stability with time was made in terms of gel flowability, stringiness, and shape retention according to a 4-grade rating system shown in Table 1 below. Superabsorbent resin compositions graded A or B are to be suitable for use as a water-absorbing material in sanitary napkins, disposable diapers, sheets for adults, tampons, absorbent cotton, etc.

TABLE 1

| Grade | Flowability | Stringiness | Shape Retention |
|---|---|---|---|
| A | non-flowable | non-stringy | unchanged |
| B | slightly flowable | slightly stringy | slightly changed |
| C | flowable | stringy | partly liquefied |
| D | flowable | stringy | largely liquefied |

Synthesis Examples 1 to 9 for the metal compounds used in Examples and Comparative Examples are shown below. All the metal compounds in Synthesis Examples were obtained in the form of a solution.

SYNTHESIS EXAMPLE 1

Synthesis of Metal Compound (I)

To an ice-cooled solution of 43.6 g of sodium gluconate in 150 g of ion-exchanged water was added dropwise 20 g of titanium tetrachloride and mixed. After confirming that the solution turned clear, about 48 g of a 30% sodium hydroxide aqueous solution was added thereto dropwise to adjust the solution to pH 7. The resulting solution was clear and faintly yellow and had a titanium content of 1.9% (calculated).

SYNTHESIS EXAMPLE 2

Synthesis of Metal Compound (II)

To 50 g of a titanium oxysulfate solution having a titanium content of 4.9% (Titanyl Sulfate Solution, produced by Kisan Kinzoku K.K.) was added dropwise 80.3 g of a 50% gluconic acid aqueous solution and mixed. About 60 g of a 30% sodium hydroxide aqueous solution was added thereto dropwise while cooling from outside to adjust the solution to pH 7. The resulting solution was clear and yellow and had a titanium content of 1.3% (calculated).

SYNTHESIS EXAMPLE 3

Synthesis of Metal Compound (III)

To a solution of 34.0 g of zirconium oxychloride octahydrate in 150 g of ion-exchanged water was added 43.6 g of sodium gluconate and mixed. About 22 g of a 30% sodium hydroxide aqueous solution was added thereto dropwise to adjust the solution to pH 7. The resulting solution was clear and faintly yellow and had a zirconium content of 3.86% (calculated).

SYNTHESIS EXAMPLE 4

Synthesis of Metal Compound (IV)

To 50 g of a titanium oxysulfate solution having a titanium content of 4.9% (Titanyl Sulfate Solution, produced by Kisan Kinzoku K.K.) were added 32.2 g of citric acid monohydrate and 25 g of ion-exchanged water and mixed. After confirming that citric acid completely dissolved, about 104 g of a 30% sodium hydroxide aqueous solution was added thereto dropwise while cooling from outside to adjust the solution to pH 7. The resulting solution was yellow and slightly turbid. The titanium content of the solution was 1.2% (calculated).

SYNTHESIS EXAMPLE 5

Synthesis of Metal Compound (V)

To 50 g of a titanium oxysulfate solution having a titanium content of 4.9% (Titanyl Sulfate Solution, produced by Kisan Kinzoku K.K.) were added 22.3 g of sodium gluconate and 50 g of ion-exchanged water and mixed. After confirming that sodium gluconate completely dissolved, about 33 g of a 30% sodium hydroxide aqueous solution was added thereto dropwise while cooling from outside to adjust the solution to pH 7. The resulting solution was clear and yellow. The titanium content of the solution was 1.6% (calculated).

SYNTHESIS EXAMPLE 6

Synthesis of Metal Compound (VI)

In 100 ml of 2-propyl alcohol was dissolved 5.36 g of DL-malic acid, and 5.68 g of titanium tetraisopropoxide was added thereto, followed by stirring under reflux for 3 hours. Then, 20 g of ion-exchanged water was added, and the stirring under reflux was continued for an additional 5 hour period. The resulting solution was white turbid and had a titanium content of 0.73% (calculated).

SYNTHESIS EXAMPLE 7

Synthesis of Metal Compound (VII)

To a solution of 14.7 g of zinc sulfate hexahydrate in 50 g of ion-exchanged water was added 80.3 g of a 50% gluconic acid aqueous solution and mixed. About 23 g of a 30% sodium hydroxide aqueous solution was added thereto dropwise to adjust the solution to pH 7. The resulting solution was clear and yellow and had a zinc content of 2.0% (calculated).

SYNTHESIS EXAMPLE 8

Synthesis of Metal Compound (VIII)

To an ice-cooled solution of 43.6 g of sodium gluconate and 150 g of ion-exchanged water was added dropwise 20 g of titanium tetrachloride and mixed. The resulting solution was colorless and clear. The titanium content of the solution was 2.4% (calculated).

SYNTHESIS EXAMPLE 9

Synthesis of Metal Compound (IX)

To 50 g of a titanium oxysulfate solution having a titanium content of 4.9% (Titanyl Sulfate Solution, produced by Kisan Kinzoku K.K.) was added 80.3 g of a 50% gluconic acid aqueous solution and mixed. The resulting solution was clear and yellow and had a titanium content of 1.9% (calculated).

The metal compound solutions obtained in Synthesis Examples 1 through 9 are tabulated below.

blown into the mixture to drive out dissolved oxygen and to displace the atmosphere with nitrogen. The flask was put in a water bath kept at 75° C.

In a separate flask 102.0 g of acrylic acid was diluted with 25.5 g of ion-exchanged water, and the solution was neutralized with 140 g of a 30% sodium hydroxide aqueous solution while cooling from outside to prepare an aqueous monomer solution. To the aqueous monomer solution were added a solution of 0.204 g of potassium persulfate in 7.5 g of ion-exchanged water as a polymerization initiator, a solution of 0.04 g of polyglycerol polyglycidyl ether (Denacol EX-512, produced by Nagase Kasei Kogyo K.K.) in 5 g of ion-exchanged water as a crosslinking agent, and 2.5 g of the metal compound (I) solution to prepare an aqueous monomer/initiator solution. Nitrogen gas was blown thereinto to remove dissolved oxygen from the aqueous monomer/initiator solution.

The aqueous monomer/initiator solution was added dropwise to the four-necked flask over a 1 hour period, followed by stirring for 15 minutes while keeping the water bath at 75° C. The reaction mixture was dehydrated azeotropically by use of a dehydrating tube to obtain a superabsorbent resin composition having a water content of 30 parts per 100 parts of the superabsorbent resin (in a dry state, hereinafter the same when referred to with respect to a water content). The composition was then dried under reduced pressure at 100° C. to yield 103 g of a superabsorbent resin composition.

The elementary analysis on the resulting superabsorbent resin composition revealed that the titanium content was 0.047% based on 100 parts of the superabsorbent resin. The holding power after centrifugal dehydration and the stability of the swollen gel of the composition were measured. The results obtained are shown in Table 3 below along with the titanium content. Prior to the evaluation, particles of 850 µm or greater were removed from the composition by means of a sieve.

TABLE 2

| Synthesis Example No. | Solution of | Hydroxy Acid (or Salt) | Polyvalent Metal Salt or Alkoxide | Metal A/Hydroxy Acid (or Salt)* | Metal Content in Metal Compound Solution (%) |
| --- | --- | --- | --- | --- | --- |
| 1 | metal compound (I) | sodium gluconate | titanium tetrachloride | 1/4 | Ti: 1.9 |
| 2 | metal compound (II) | gluconic acid | titanium oxysulfate | 1/4 | Ti: 1.3 |
| 3 | metal compound (III) | sodium gluconate | zirconium oxychloride | 1/4 | Zr: 3.9 |
| 4 | metal compound (IV) | citric acid | titanium oxysulfate | 1/3 | Ti: 1.2 |
| 5 | metal compound (V) | sodium gluconate | titanium oxysulfate | 1/2 | Ti: 1.6 |
| 6 | metal compound (VI) | DL-malic acid | titanium tetraisopropoxide | 1/4 | Ti: 0.73 |
| 7 | metal compound (VII) | gluconic acid | zinc sulfate | 1/4 | Zn: 2.0 |
| 8 | metal compound (VIII) | sodium gluconate | titanium tetrachloride | 1/4 | Ti: 2.4 |
| 9 | metal compound (IX) | gluconic acid | titanium oxysulfate | 1/4 | Ti: 1.9 |

Note:
*Molar ratio

EXAMPLE 1

In a 1000 ml four-necked flask equipped with a stirrer, a reflux condenser, a dropping funnel, and a tube for nitrogen gas introduction were charged 40 ml of cyclohexane and 0.625 g of ethyl cellulose (Ethyl Cellulose N-100, produced by Hercules Powder Co.) as a dispersant. Nitrogen gas was

EXAMPLE 2

Polymerization was carried out to obtain a superabsorbent resin composition in the same manner as in Example 1, except for replacing 2.5 g of the metal compound (I) solution with 2.0 g of the metal compound (III) solution. The resulting resin composition was evaluated in the same manner as in Example 1. The results obtained are shown in Table 3.

EXAMPLE 3

Polymerization was carried out to obtain a superabsorbent resin composition in the same manner as in Example 1, except for replacing 0.625 g of ethyl cellulose used as a dispersant with 1.5 g of a 25% solution of sodium polyoxyethylene lauryl ether sulfate (average number of moles of ethylene oxide added: 2), increasing the amount of the polyglycerol polyglycidyl ether (Denacol EX-512, produced by Nagase Kasei Kogyo K.K.) used as a crosslinking agent from 0.04 g to 0.06 g, and replacing 2.5 g of the metal compound (I) solution with 4.0 g of the metal compound (II) solution. The resulting superabsorbent resin composition was evaluated in the same manner as in Example 1. The results obtained are shown in Table 3.

EXAMPLE 4

Polymerization was carried out to obtain a superabsorbent resin composition in the same manner as in Example 1, except for replacing 2.5 g of the metal compound (I) solution with 3.2 g of the metal compound (IV) solution. The resulting resin composition was evaluated in the same manner as in Example 1. The results obtained are shown in Table 3.

EXAMPLE 5

Polymerization was carried out to obtain a superabsorbent resin composition in the same manner as in Example 1, except for replacing 2.5 g of the metal compound (I) solution with 2.5 g of the metal compound (VIII) solution. The resulting resin composition was evaluated in the same manner as in Example 1. The results obtained are shown in Table 3.

EXAMPLE 6

Polymerization was carried out to obtain a superabsorbent resin composition in the same manner as in Example 3, except for replacing 4.0 g of the metal compound (II) solution with 2.7 g of the metal compound (IX) solution. The resulting resin composition was evaluated in the same manner as in Example 1. The results obtained are shown in Table 3.

EXAMPLE 7

Polymerization was carried out to obtain a superabsorbent resin composition in the same manner as in Example 1, except that the metal compound (I) solution was not added to the aqueous monomer solution to be polymerized. Instead, 1.5 g of the metal compound (I) solution was added dropwise to the four-necked flask over 5 minutes after the polymerization and before azeotropic dehydration. The resulting resin composition was evaluated in the same manner as in Example 1. The results obtained are shown in Table 3.

EXAMPLE 8

Polymerization was carried out to obtain a superabsorbent resin composition in the same manner as in Example 3, except that the metal compound (II) solution was not added to the aqueous monomer solution to be polymerized. Instead, 3.0 g of the metal compound (II) solution was added dropwise to the four-necked flask over 5 minutes after the polymerization and before azeotropic dehydration. The resulting resin composition was evaluated in the same manner as in Example 1. The results obtained are shown in Table 3.

EXAMPLE 9

Polymerization was carried out to obtain a superabsorbent resin in the same manner as in Example 1, except that the metal compound (I) solution was not added to the aqueous monomer solution. The resulting superabsorbent resin was put in a twin-cylinder kneader, and 10 g of the metal compound (V) solution was uniformly sprayed onto the superabsorbent resin while stirring. Then, the mixture was dried under reduced pressure of 50 Torr at 80 to 100° C. to obtain a superabsorbent resin composition. The resulting resin composition was evaluated in the same manner as in Example 1. The results obtained are shown in Table 3.

EXAMPLE 10

Polymerization was carried out to obtain a superabsorbent resin in the same manner as in Example 3, except that the metal compound (II) solution was not added to the aqueous monomer solution. The resulting superabsorbent resin was put in a twin-cylinder kneader, and 3.0 g of the metal compound (II) solution was uniformly sprayed onto the superabsorbent resin while stirring. Then, the mixture was dried under reduced pressure of 50 Torr at 80 to 100° C. to obtain a superabsorbent resin composition. The resulting resin composition was evaluated in the same manner as in Example 1. The results obtained are shown in Table 3.

EXAMPLE 11

Polymerization was carried out to obtain a superabsorbent resin in the same manner as in Example 3, except that the metal compound (II) solution was not added to the aqueous monomer solution. Separately, 14.5 g of the metal compound (VI) solution was thoroughly dried at 80° C. under reduced pressure and ground in a mill to obtain white powder. The resulting superabsorbent resin and the white powder obtained from the metal compound (VI) solution were put in a twin-cylinder kneader and thoroughly mixed to obtain a superabsorbent resin composition. The resulting resin composition was evaluated in the same manner as in Example 1. The results obtained are shown in Table 3.

COMPARATIVE EXAMPLE 1

Polymerization was carried out to obtain a superabsorbent resin in the same manner as in Example 1, except that the metal compound (I) solution was not added to the aqueous monomer solution. The resulting superabsorbent resin was evaluated in the same manner as in Example 1. The results obtained are shown in Table 3.

COMPARATIVE EXAMPLE 2

Polymerization was carried out to obtain a superabsorbent resin in the same manner as in Example 3, except that the metal compound (II) solution was not added to the aqueous monomer solution. The resulting superabsorbent resin was evaluated in the same manner as in Example 1. The results obtained are shown in Table 3.

COMPARATIVE EXAMPLE 3

Polymerization was carried out to obtain a superabsorbent resin composition in the same manner as in Example 1, except for replacing 2.5 g of the metal compound (I) solution with a solution consisting of 0.8 g of a titanium oxysulfate having a titanium content of 4.9% (Titanyl Sulfate Solution, produced by Kisan Kinzoku K.K.) and 2.2 g of ion-exchanged water. The resulting superabsorbent resin composition was evaluated in the same manner as in Example 1. The results obtained are shown in Table 3.

COMPARATIVE EXAMPLE 4

Polymerization was carried out to obtain a superabsorbent resin composition in the same manner as in Example 1, except for replacing 2.5 g of the metal compound (I) solution with 4.0 g of the metal compound (VII) solution. The resulting superabsorbent resin composition was evaluated in the same manner as in Example 1. The results obtained are shown in Table 3.

COMPARATIVE EXAMPLE 5

Polymerization was carried out to obtain a superabsorbent resin in the same manner as in Example 1, except that the metal compound (I) solution was not added to the aqueous monomer solution. The resulting superabsorbent resin was put in a twin-cylinder kneader, and 0.3 g of titanic sulfate dihydrate (produced by Katayama Kagaku Kogyo K.K.) was added thereto, followed by thoroughly stirring to obtain a superabsorbent resin composition. The resulting resin composition was evaluated in the same manner as in Example 1. The results obtained are shown in Table 3.

TABLE 3

| Example No. | Metal Compound | Metal Content (part*) | Holding Power after Centrifugal Dehydration (g/g) | Swollen Gel Stability |
|---|---|---|---|---|
| Example 1 | (I) | 0.05 | 44 | A |
| Example 2 | (III) | 0.08 | 45 | A |
| Example 3 | (II) | 0.05 | 48 | B |
| Example 4 | (IV) | 0.04 | 48 | B |
| Example 5 | (VIII) | 0.05 | 44 | A |
| Example 6 | (IX) | 0.05 | 48 | B |
| Example 7 | (I) | 0.03 | 42 | A |
| Example 8 | (II) | 0.06 | 44 | A |
| Example 9 | (V) | 0.07 | 42 | A |
| Example 10 | (II) | 0.04 | 45 | B |
| Example 11 | (VI) | 0.01 | 45 | B |
| Compara. Example 1 | — | — | 43 | D |
| Compara. Example 2 | — | — | 47 | D |
| Compara. Example 3 | titanium oxysulfate | 0.04 | 43 | C |
| Compara. Example 4 | (VII) | 0.08 | 47 | D |
| Compara. Example 5 | titanic sulfate | 0.04 | 42 | C |

Note:
*Per 100 parts by weight of a superabsorbent resin.

This application claims the priority of Japanese Patent Application Nos. 9-19232 filed Jan. 31, 1997, and 9-239319 filed Sep. 4, 1997, which are incorporated herein by reference.

What is claimed is:

1. A superabsorbent resin composition comprising (A) a crosslinked polyacrylic acid salt and (B) a metal compound obtained by mixing (i) an α-hydroxy acid selected from the group consisting of gluconic acid, citric acid, isocitric acid, alloisocitric acid, lactic acid, hydroxyacetic acid, malic acid and tartaric acid, or a salt thereof, and (ii) a titanium salt selected from the group consisting of a sulfate and an oxysulfate, and wherein the Δ-hydroxy acid or the salt thereof is present in an amount of not less than twice the molar quantity of titanium in the titanium salt. having at least one metal that is titanium.

2. The superabsorbent resin composition according to claim 1, wherein said α-hydroxy acid is gluconic acid, citric acid, or a mixture of gluconic acid and citric acid.

3. The superabsorbent resin composition according to claim 1, wherein said metal compound as component (B) has a content of said metal of 0.001 to 1 part by weight per 100 parts by weight of said superabsorbent resin as component (A).

4. The superabsorbent resin composition according to claim 1, wherein said crosslinked polyacrylic acid salt as component (A) has a water holding power of 35 g/g or more when swollen with physiological saline for 30 minutes and then centrifugally dehydrated.

5. A method for producing a superabsorbent resin composition comprising polymerizing a water-soluble vinyl monomer in the presence of a metal compound as component (B), to thereby provide a crosslinked polyacrylic acid salt as component (A), wherein said metal compound as component (B) is obtained by mixing a hydroxy acid or a salt thereof and a polyvalent metal salt or polyvalent metal alkoxide having at least one metal that is titanium.

6. The method for producing a superabsorbent resin composition according to claim 4, wherein said water-soluble vinyl monomer comprises at least 50% by weight of at least one member selected from the group consisting of acrylic acid, an alkali metal acrylate, and ammonium acrylate.

7. The method for producing a superabsorbent resin composition according to claim 4, wherein said metal compound as component (B) has a content of said metal of 0.001 to 1 part by weight per 100 parts by weight of said water-soluble vinyl monomer.

8. The method for producing a superabsorbent resin composition according to claim 5, wherein said hydroxy acid is an α-hydroxy acid.

* * * * *